United States Patent [19]
Cheng et al.

[11] Patent Number: 5,772,592
[45] Date of Patent: Jun. 30, 1998

[54] METHOD FOR DIAGNOSING AND MONITORING OSTEOPOROSIS

[76] Inventors: Shu Lin Cheng, 7927 Farnifold, #2, Germantown, Tenn. 38138; Jussi Timonen, Soidintie 5 C, FIN-40630, Jyväskylä, Finland; Harri Suominen, Soidintie, 1, #3, FIN-40630 Jyväskylä, Finland; Jari Toivanen, Ylälahdentie 1, #4, FIN-40500 Jyväskylä, Finland

[21] Appl. No.: 587,108

[22] Filed: Jan. 8, 1996

[51] Int. Cl.$^6$ ..................................................... A61B 5/00
[52] U.S. Cl. ............................................. 600/407; 378/54
[58] Field of Search ............................. 128/653.1, 653.2, 128/781; 378/54–56, 112, 197, 205, 207, 209, 98.9; 250/370.08, 370.09, 402; 600/407, 410, 594

[56] References Cited

U.S. PATENT DOCUMENTS

| | | | |
|---|---|---|---|
| 4,200,797 | 4/1980 | Bax | 250/402 |
| 5,132,995 | 7/1992 | Stein | 378/56 |
| 5,247,934 | 9/1993 | Wehrli et al. | 128/653.1 |
| 5,533,084 | 7/1996 | Mazess | 378/54 |

OTHER PUBLICATIONS

Estimation of Structural and Geometrical Properties of Cortical Bone by Computerized Tomography in 78–Year–old Women by Sulin Cheng et al, dated Jan. 9, 1995, vol. 10, pp. 139–144 and 146–148 in the Journal of Bone and Mineral Research.

*Primary Examiner*—Marvin M. Lateef
*Assistant Examiner*—Eleni Mantis Mercader
*Attorney, Agent, or Firm*—Fildes & Outland, P.C.

[57] ABSTRACT

A method for diagnosing and monitoring osteoporosis includes the steps of obtaining volumetric bone mineral density and cross-sectional area information of a bone of a patient utilizing computerized tomography, displaying the information in matrix image form wherein each pixel indicates the density of the bone tissue in the image area at that point, distinguishing pixels depicting bone tissue from the rest of the image utilizing a lower-limit criteria, calculating the mass distribution of bone tissue meeting and exceeding the criteria, and quantifying the condition of the patient's bone tissue as a function of the calculated mass distribution of bone tissue.

8 Claims, 6 Drawing Sheets

5,772,592

METHOD FOR DIAGNOSING AND MONITORING OSTEOPOROSIS

FIELD OF THE INVENTION

This invention relates to a method for diagnosing and monitoring osteoporosis.

BACKGROUND OF THE INVENTION

Bone mineral content (BMC) and density (BMD) measurements have been widely used in vivo to predict fracture risk. However, the occurrence of fractures is not dependent on bone mass and density alone; bone structure and geometry also contribute to the integrity of the skeleton.

Previous studies have shown that perforations during the remodeling process lead to the loss of vertebral bone biomechanical strength with age that is much more pronounced than the loss of absolute bone mass. Myers et al., found that the in vitro failure force of the distal radius correlated with the distal radius width, cross-sectional area, and principal area moments of inertia (geometric indeices of bone rigidity), but not with BMC or BMD. Evidence from rat femora also showed that the strength and stiffness of the integrated diaphyses depend on both the cross-sectional moment of inertia and body weight, but not on BMD. Recruits with low area moments of inertia of the tibia were found to have higher stress fracture morbidity than those with a high area moment of inertia in vivo.

In general, estimation of bone strength requires knowledge of the material and geometrical properties of bone as well as its loading conditions. However, the relative contribution of each of these factors to overall bone strength is, for the most part, unknown. New methods have therefore been developed that address not only BMC and BMD but also the material and geometrical properties of bone. Such methods have not, however, been frequently applied to elderly women. Neither have the previous studies on the resistance of cortical bone to bending assessed the true moments of inertia, i.e., taken into account how the bone mass is actually distributed along the cross-sectional area of the bone.

Osteoporosis, the increase of the brittleness of bones, is a problem in the health of aging people—especially women. Osteoporotic fractures and the complications related to them significantly increase the costs of health care as the proportion of old people in the population increases.

Osteoporosis is generally investigated by measuring the bone mineral content and/or density. It is not possible to determine the real density of bones by means of the methods used; with the exception of computerized tomography.

Measurements of bone density do not as such give sufficient information on the various properties of bones. In particular, reliable information is not available on the fracture risk of a bone.

SUMMARY OF THE INVENTION

The intention of this invention is to create a method for the estimation of the geometric and mechanical properties of bones and to create a new, simple method, which is safe to the patient, of measuring the structure and strength of bones.

In the method in accordance with the invention, quantitative computerized tomography (QCT) is used, by means of which initially the geometry and density distribution of a bone is obtained. From the image data obtained, one or more quantities are calculated, which depict the osteoporotic state of the skeletal structure of the patient better than before.

Any cortical bone can be used as the object of investigation. The femur and tibia have been shown in clinical experiments to be highly suitable objects of investigation.

In the QCT images obtained, the value of each pixel represents the density of the tissue at the point in question. By means of this—by selecting a suitable lower-limit criterium—it is possible to distinguish the substance of the bone from the rest of the image. Even inside the bone, the density still vanes, which is taken into account in the method of calculation used.

These and other features and advantages of the invention will be more fully understood from the following detailed description of the invention taken together with the accompanying drawings.

DETAILED DESCRIPTION OF THE INVENTION

Figure 1:
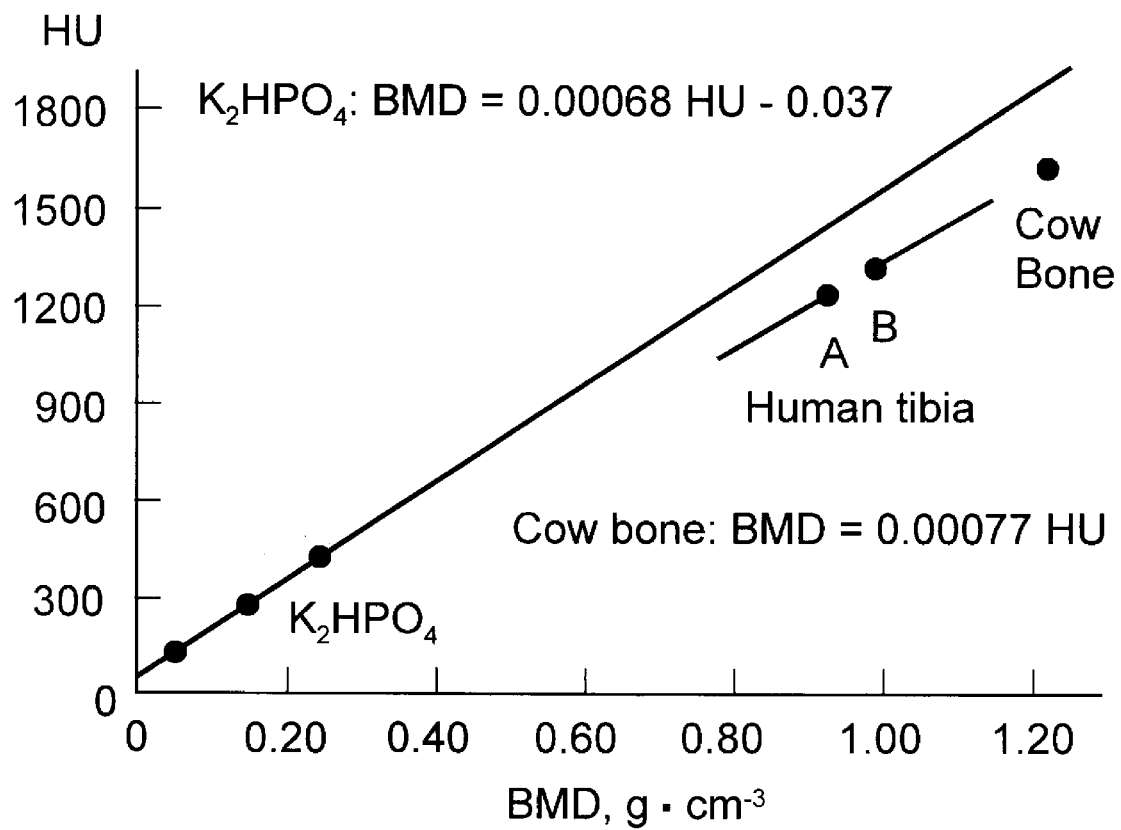
FIG. 1. Relationship between the Hounsfield units (HU) and density of $K_2HPO_4$ and cow bone in CT measurements. The figure also shows the results (mean, SD) for the tibia at the sections A and B of 78-year-old women when calculated on the basis of the cow bone ash density.

The subjects were selected from the population of 78-year-old women resident in the city of Jyväskylä in 1992 according to their calcaneal bone mineral density as previously measured by the $^{125}I$-photon absorption method. At that time, 30 women had BMD values>0.160 g·cm$^{-3}$ (about 1 SD above the population mean) and 27 women had BMD values<0.100 g·cm$^{-3}$ (about 1 SD below the mean). A letter was sent to 23 women selected randomly from the high BMD group and 22 women from the low BMD group. Two subjects refused, 2 were ill during the tests, 4 failed to appear and bone measurements were not obtained for 1 person. The high BMD group ($0.190\pm0.025$ g·cm$^{-3}$) thus comprised 19, and the low BMD group ($0.077\pm0.012$ g·cm$^{-3}$) 17, subjects. The mean calcaneus BMD value in the high BMD group was similar to that of healthy middle-aged women. The low BMD group had calcaneus BMD values at a level for high fracture risk. An informed consent was obtained in advance from all the subjects.

Body weight and body mass index were higher in the high BND group than in the low BMD group (Table 1). Body height was not different between the two groups.

TABLE 1

Physical characteristics and the cross-sectional area and BMD at the sections A and B of the tibia at >250 HU level in the high and low calcaneus BMD groups of 78-year-old women (mean ± SD)

| Variables | High BMD group (n = 19) | Low BMD group (n = 17) |
|---|---|---|
| Body height (cm) | 153.2 ± 5.3 | 156.3 ± 7.5 |
| Body weight (kg) | 68 ± 10.1 | 60.5 ± 12.9 |
| Body mass index | 29 ± 4.5 | 24.7 ± 4.6 |
| Tibia CSA A | 334 ± 33 | 295 ± 44 |
| (mm$^2$) B | 297 ± 35 | 270 ± 44 |
| Tibia BMD A | 1.031 ± 0.072 | 0.816 ± 0.127 |
| (g/cm$^3$) B | 1.097 ± 0.076 | 0.88 ± 0.14 |

Information about the subjects' habitual physical activity, smoking and drinking habits, and menopausal history were collected by a postal questionnaire and interview. The women in the high BMD group had been physically more active in their earlier life span than those in the low BMD group (age periods 20–49, p<0.01–0.05). There were no differences in current physical activity, smoking, drinking, menopausal age or number of gravidities between the high and low BMD groups. After the first bone measurements, no one was under medication or treatment on osteoporosis in either of the groups.

The fracture history of the subjects was also collected by a postal questionnaire and checked against X-ray records at the health center of the city of Jyväskylä and in the Central Hospital of Central Finland. Five (26%) of the subjects in the high BMD group and 12 (71%) of the subjects in the low BMD group had fractured a bone at least once after the age of 50. The fractured bone sites were mainly at the metacarpi, upper arm and lower leg or ankle. A fall was the reason for all fractures.

A CT scanner (Siemens SOMATOM CR) was used to determine the volumetric bone mineral density and cross-sectional area (CSA, defined as the total surface area of bone material in a plane perpendicular to the bone long axis) at two sections of the tibia. To assure a geometrically similar section in all axes along the leg, the leg length (L) was defined as the distance from the lateral condyle of the tibia to the lateral malleolus of the fibula. The distance from the tibial tuberosity distally to section A was then determined as L·0.33 ( 9.5 ±0.7 cm) and further down to section B as L·0.53 (15.5±1.2 cm). The sections were the same as those used for the elastic wave velocity measurements performed at the same time. The system parameters employed in this study were as follows: a pixel size at X and Y of 0.2 mm, slice thickness of 2 mm, pixel matrix of 256×256, and exposure factors of 125 kV, 500 mA and 7 s.

Data were analyzed on a HP computer by using a map and image processing software program. Every pixel of >250 Hounsfield units (HU) in the original image was included as bone and then the density and CSA numerically calculated. Simulated bone standards, i.e. known concentrations of $K_2HPO_4$ (0.05, 0.15 and 0.25 g·cm$^{-3}$) in plastic containers, were scanned daily to determine the relationship between the attenuation coefficient $\mu$ (HU) and density (FIG. 1). In addition, a piece of frozen cow tibia bone with soft tissues corresponding to a human tibia was placed between the legs of the subject and scanned simultaneously with the subject as a standard to cover the higher cortical densities and to control any eventual variations in measuring technique. Ash-apparent-density was calculated as ash weight/sample volume(23). There was a linear relationship between HU and density for $K_2HPO_4$ and cow bone, the attenuation of bone being, however, 15% lower than that of $KBHPO_4$ It has also been shown previously(24) that a change of 1 mg·cm$^{-3}$ in bone mineral concentration would correspond to a change of 1.14–1.17 mg·cm$^{-3}$ in $K_2HPO_4$ concentration. Consequently, the tibia bone density was calculated on the basis of the cow bone ash density (FIG. 1).

The coefficient of variation (CV) for repeated measurements of the CT density was on average 2.1% (0.02 g·cm$^{-3}$) for the cow bone and less than 3% (0.03 g·cm$^{-3}$) for the human tibia. According to our experience, the variation is mainly due to the differences in positioning of the bone during the measurement.

The CSA of the cow bone was also measured directly (Summagraphics 10, Data Tablet/Digitizer, Fairfield, USA). In accordance with previous studies, CT showed a 10.7% overestimation of CSA compared to the directly measured anatomic CSA. This may be due to that bone will be enlarged by the more radiolucent surrounding tissues in CT-CSA, which might be related to how the back-projection is filtered for generating images in CT technique. Consequently, we corrected this error in the CT measurements, although the small systematic difference would not actually affect the comparison of the low and high BMD group in the present study. The CV of the CT-CSA was 0.5% for the cow bone and less than 3% for the human tibia.

The area moments of inertia of the tibia have previously been used to characterize its elastic properties and its susceptibility to fracture. However, the use of area moment of inertia to predict material rigidity is accurate only for a homogeneous material. In general, for non-homogeneous material, it is the true moment of inertia which should be used. The use of area moments of inertia can, of course, be justified, in case the variations in density of a material are small.

In this study computerized tomography was used to record the characteristics of bone, thus allowing measurement of the local density of the bone under consideration and its cross-sectional variation, and also able to calculate both the true and area moments of inertia, and to compare their predictive capacity with regard to BNM group. We also analyzed the role of local density variation by comparing area moments of inertia with weighted (with respect to density) area moments of inertia.

Figure 2:
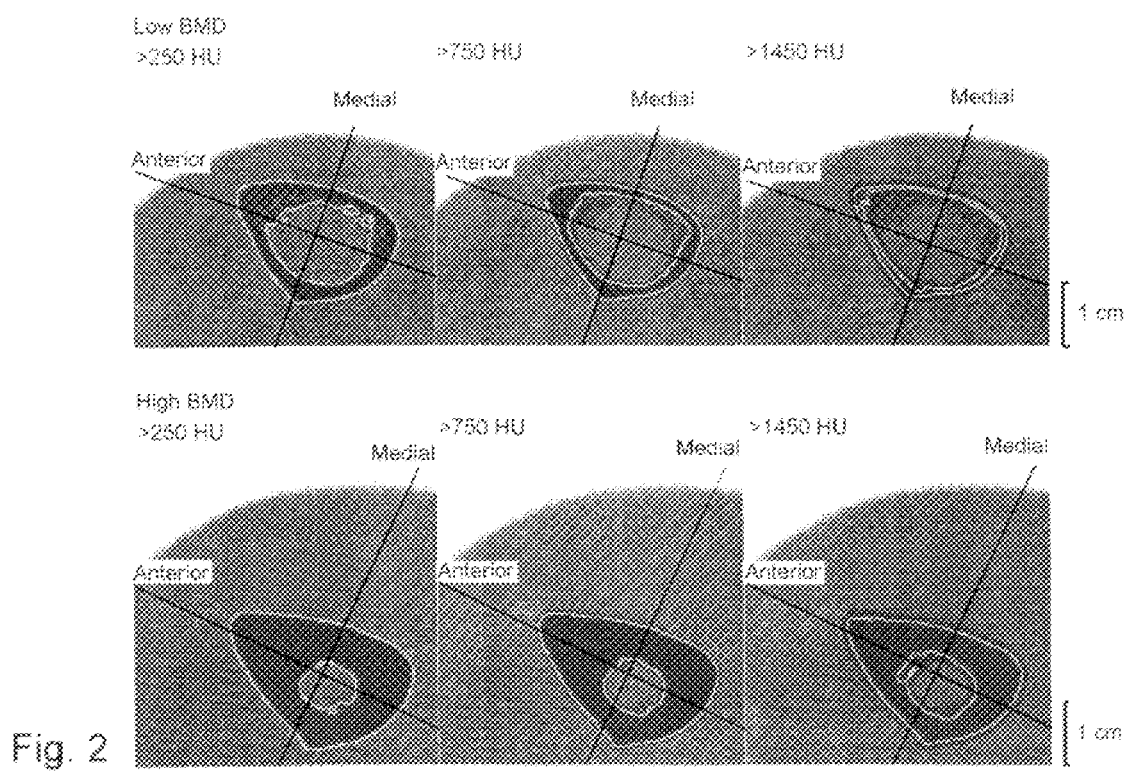
FIG. 2. An example of the determination of the center of mass and the anterior-posterior and medial-lateral axes for cross-sectional areas representing different densities in the CT Scan. Cross section through the middle shaft of the right leg. Sectioned surfaces are viewed distally.

Both the true moments of inertia and the two area moments of inertia of the mid-part of the tibia (section A and section B) were calculated numerically from the CT scans, firstly with respect to two orthogonal directions: anterior-posterior ($I_{ap}$) and medial-lateral ($I_{ml}$). The anterior-posterior (ap) axis (called the y-axis) was defined to coincide with the direction of the widest tibia width in the anterior-posterior direction which goes through the center of mass of the cross section, and the medial-lateral (ml) axis (called the x-axis) was defined as perpendicular to the y-axis (FIG. 2). All moments of inertia were determined from the expressions $$I_{ml} = I_{yy} = \int_{A_b} y^2 w dA_b, \quad I_{ap} = I_{xx} = \int_{A_b} x^2 w dA_b$$

in which w is given by $$w = \begin{cases} 1, & \text{area moment of inertia} \\ \rho(g \cdot cm^{-3}), & \text{moment of inertia} \\ \rho A_b/\int \rho dA_b, & \text{scaled area moment of inertia} \end{cases}$$

Here the area $A_b$ is determined from the condition HU>250 HU. The moments of inertia have also been determined for different values of $HU_{min}$ i.e. for HU>450, HU>650, HU>850, HU>1050, HU>1250 and HU>1450. In the following, the area moments of inertia, which excluded the effects of bone mass distribution and regarded bone as a homogeneous material, are denoted by $I^a$; the scaled area moments of inertia, which did not include the total bone mass, by $I^{sa}$; and the true moments of inertia by $I^p$.

Secondly, the principal true ($I^p_{max}$, $I^p_{min}$) and area moments of inertia ($I^a_{max}$, $I^a_{min}$, $I^{sa}_{max}$ and $I^{sa}_{min}$) for the two sections, and the angle of rotation (R) of the principal axes, were calculated from the expressions $$I_{min} = \frac{1}{2}\left(I_{xx} + I_{yy} - \sqrt{(I_{yy} - I_{xx})^2 + 4I_{xy}^2}\right)$$

$$I_{max} = \frac{1}{2}\left(I_{xx} + I_{yy} + \sqrt{(I_{yy} - I_{xx})^2 + 4I_{xy}^2}\right)$$

$$R = \frac{1}{2}\arctan\frac{-2I_{xy}}{I_{yy} - I_{xx}},$$

where $I_{xy}$ is the cross product of inertia of the ap and ml axes. The angle R was calculated as the angle between the $I_{max}$ axis and the ap axis in the clockwise direction. $I_{max}$ is related to the direction of the greatest and $I_{min}$ to the smallest flexural rigidity.

In an attempt to ascertain whether and how the bone mass and density distribution at the measured scans differ between the two groups of women, the mass spectrum and the density spectrum were also determined.

The bone mass spectrum $ms(\alpha)$ as a discrete function of the angle a with respect to the x-axis defined above was determined by $$ms(\alpha) = \int_0^\infty \left[\int_{n\Delta\alpha}^{(n+1)\Delta\alpha} \rho(r,\alpha)d\alpha\right] rdr,$$

where n is an integer, n=0,1, . . . , $2\pi/\Delta\alpha - 1$ such that $n\Delta\alpha \leq \alpha < (n+1)\Delta\alpha$, and the constant $\Delta\alpha$ is chosen to be $5\pi/180$ (or 5°). Here $\rho(r,\alpha)$ is the density of the bone at point $(r,\alpha)$ as determined by CT. The variables r and $\alpha$ are the polar coordinates which intersect, with the center of mass (CM) as the origin. Notice that $ms(\alpha)$ is the mass of a sector around angle $\alpha$ of angular width $\Delta\alpha$.

The density spectrum $ds(r)$, i.e. the average density in an annulus around the CM, was determined as a discrete function of distance r from the CM, by $$ds(r) = \frac{\int_{i\Delta r}^{(i+1)\Delta r}\int_0^{2\pi} d(r,\alpha)rd\alpha dr}{\int_{i\Delta r}^{(i+1)\Delta r}\int_0^{2\pi} \chi_B(r,\alpha)rd\alpha dr},$$

when $\int_{i\Delta r}^{(i+1)\Delta r}\int_0^{2\pi} \chi_B(r,\alpha)rd\alpha dr \neq 0$ $ds(r)=0$, otherwise
where n is an integer such that $n\Delta r \leq r < (n+1)\Delta r$, and $\chi_B(r,\alpha)$ is the characteristic function for the set B (B is the bone), i.e.

$$\chi_B(r,\alpha) = \begin{cases} 1, & \text{when}(r,\alpha)\epsilon B \\ 0, & \text{otherwise.} \end{cases}$$

For the increment $\Delta r$ we chose $\Delta r=0.5$ mm.

The statistical significance of differences between the two independent groups and of correlation coefficients were determined by Students t-test (two-tailed). The relationships between the geometrical properties, BMP and body weight were examined by Pearson's product moment correlation coefficients. The analysis of covariance and partial correlation coefficients were applied to control the effect of body weight on BMD and geometrical properties. Chi-square ($X^2$) was used to test the physical activity differences between the groups.

The mid-tibial shaft where sections A and B are located, consist mostly cortical bone. The low BMD group had a significantly lower BMD at sections A and B (21% and 20%, respectively) and a lower bone CSA at both sections (12% and 9%, respectively) compared to values in the high BMD group (Table 1).

Figure 3A:
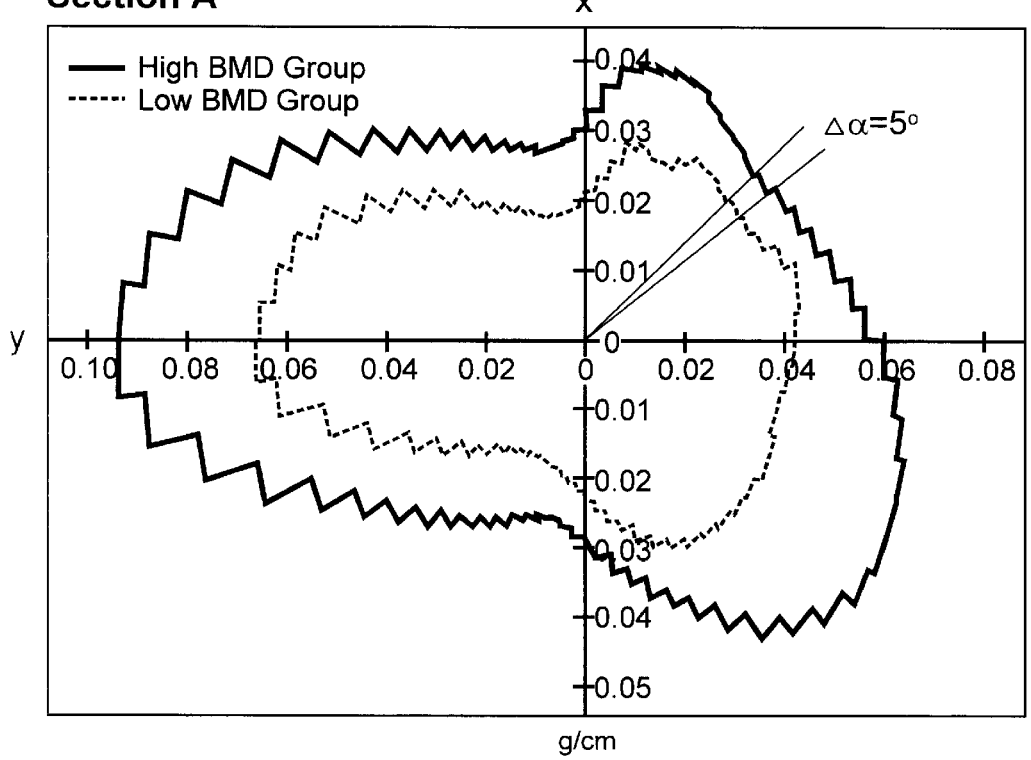
FIG. 3. The bone mass spectrum (mean) showing the angular distribution (around the mass center) of bone mass in the high and low BMD groups at sections A and B. x and y are the principal axes. x is related to the medial-lateral direction (up to down) and y to the anterior-posterior direction (left to right). The distance of the curve from the origin is the mass in grams at a 1 cm-thick section. 5° interval ($\Delta\alpha$) is used for each sector.
Figure 3B:
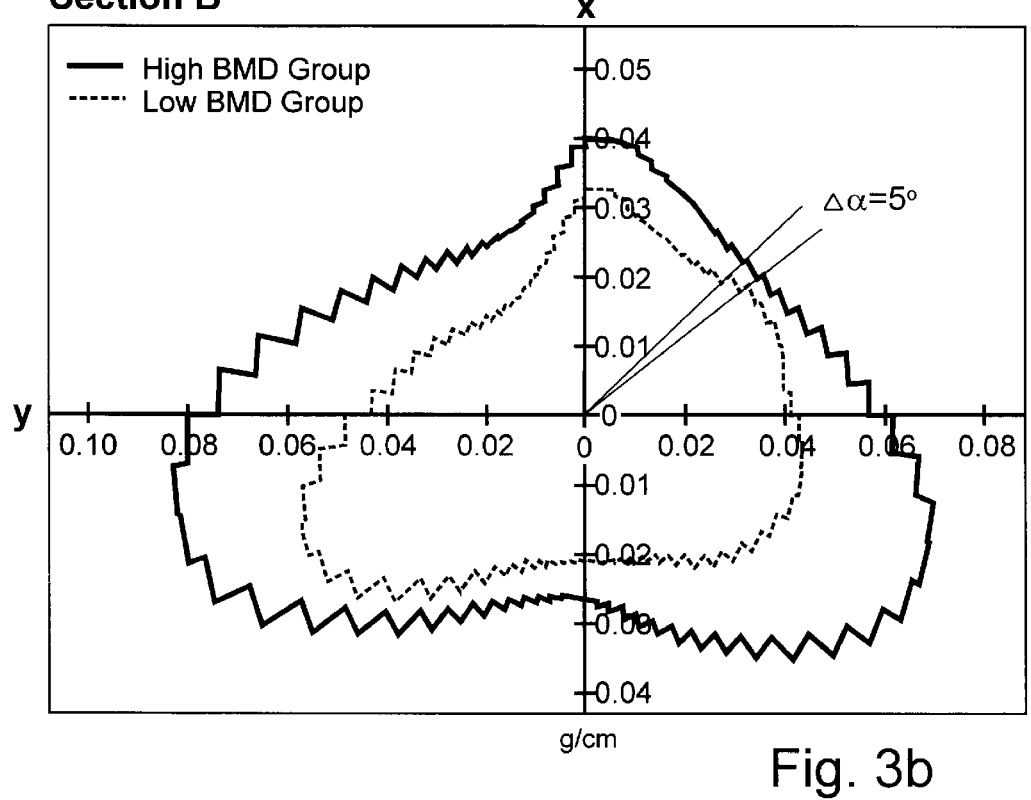

The angle distribution of bone mass at sections A and B for each group is shown in FIG. 3. The bone mass is mainly located in the ap direction for both groups and at both sections. The differences in the distribution between the high and low BMD groups were significant around the direction of the maximum principal axis, especially in the anterior part. However, both groups had a similar basic pattern of mass distribution at the measured sections.

Figure 4A:
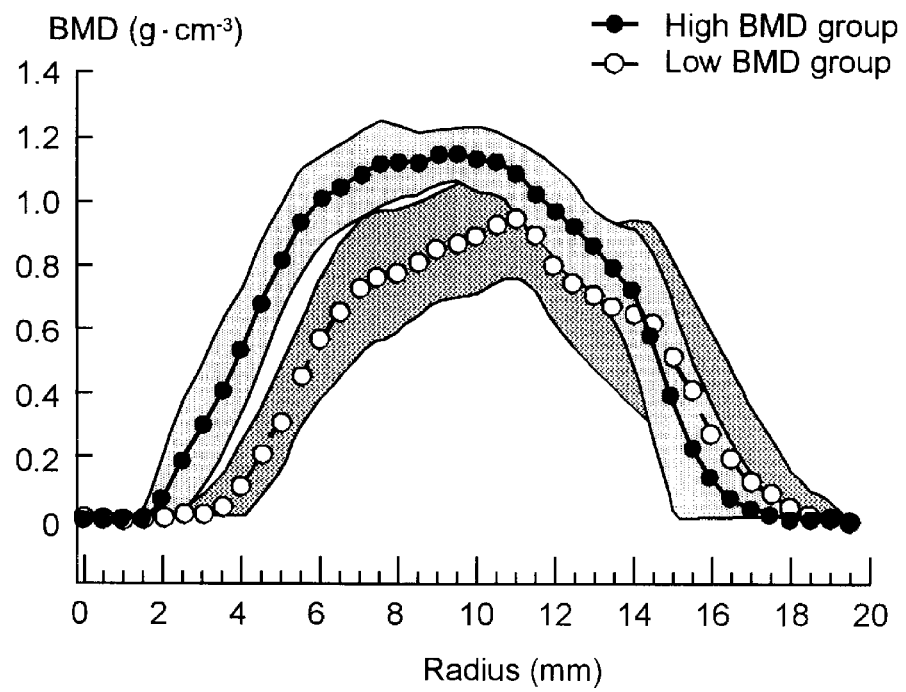
FIG. 4. The density spectrum (mean, SD) showing the density versus radius from the mass center (CM) in the high and low BMD groups at sections A and B. The average density in an annulus around the CM is determined as a discrete function of the distance from the CM. For the increment $\Delta r = 0.5$ mm is used.
Figure 4B:
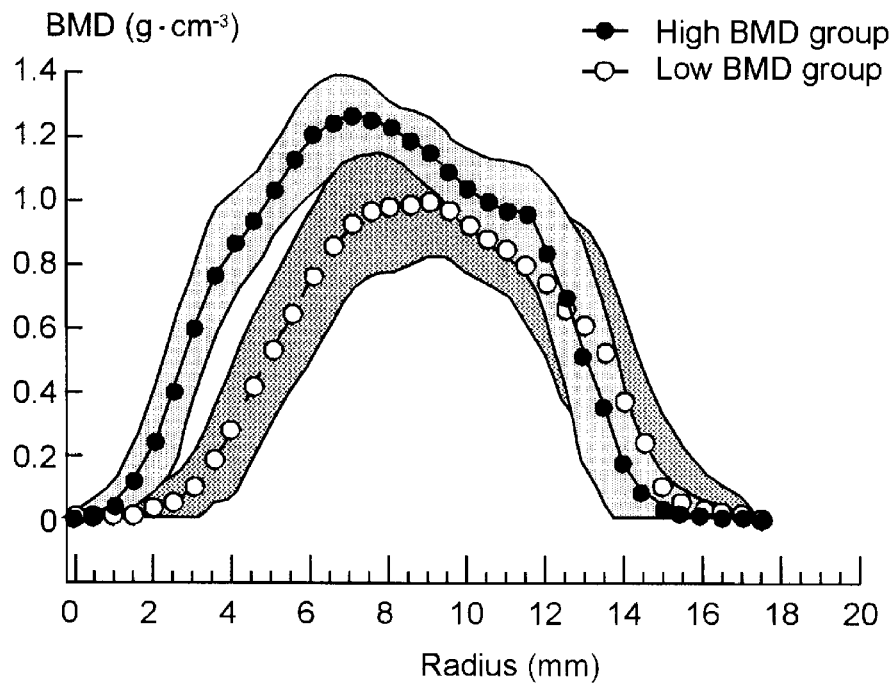

FIG. 4 shows the distribution of bone density as a function of the distance from the center of mass through the diaphyseal wall at sections A and B for each group. It is evident that the subjects in the low BMD group had lost their bone density mainly from the endosteal surface of the bone. The differences between the high and low BMD groups were significant in the annulus between 2.5 mm and 13 mm around CM (p<0.001–0.05) at section A, and in the annulus between 1.5 mm and 11.5 mm (p<0.001–0.05) at section B, respectively.

Figure 5:
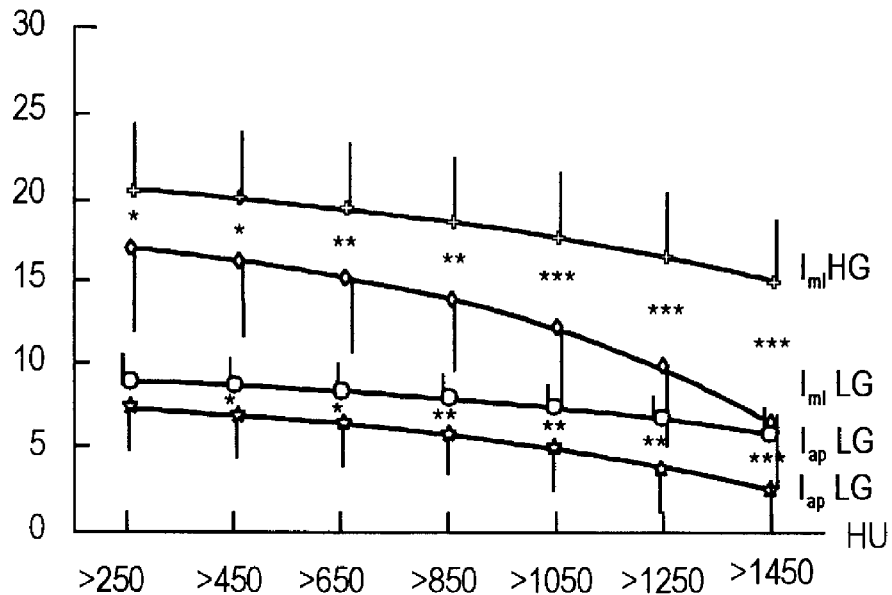
FIG. 5. Moments of inertia of the tibia at sections A and B of 78-year-old women as determined for different values of BMD (HU) in the high (HG) and low (LG) BMD groups ($^*p<0.05$, $^{}p<0.01$, $^{*}p<0.001$).,$I_{ml}^\delta$ is the moment of inertia in the medial-lateral direction and $I_{ap}^\delta$ is the moment of inertia in the anterior-posterior direction.
Figure 5:
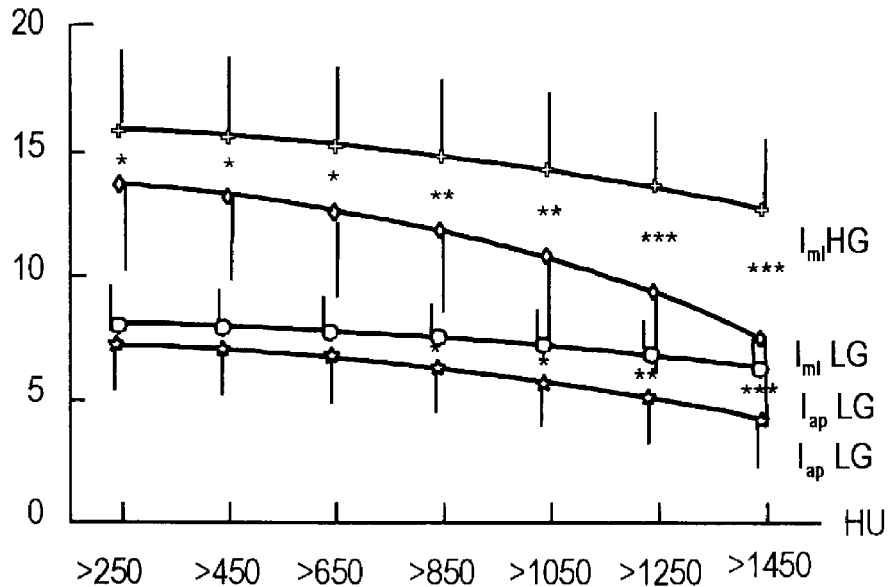
Figure 6:
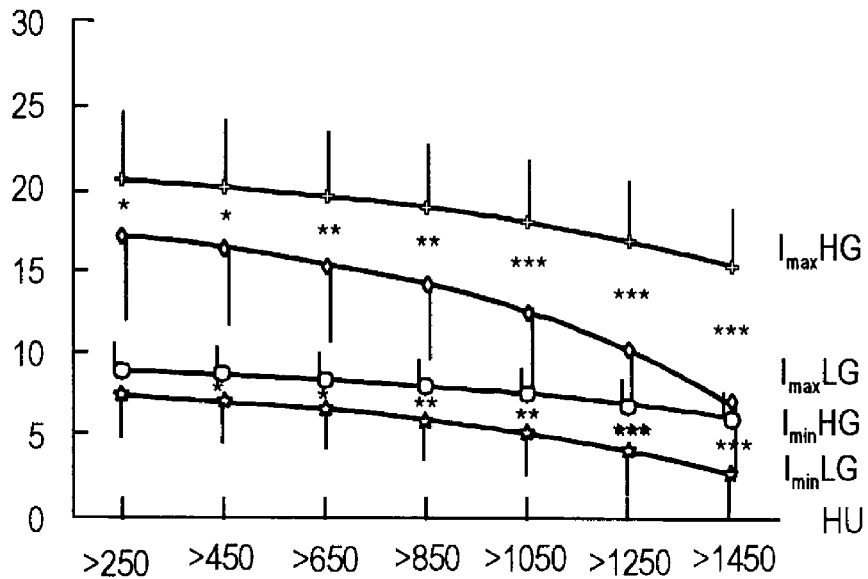
FIG. 6. The principal moments of inertia ($I_{max}^\delta$, $I_{min}^\delta$) of the tibia at sections A and B of 78-year-old women as determined for different values of BMD (HU) in the high (HG) and low (LG) BMD groups ($^*p<0.05$, $^{}p<0.01$, $^{*}p<0.001$).
Figure 6:
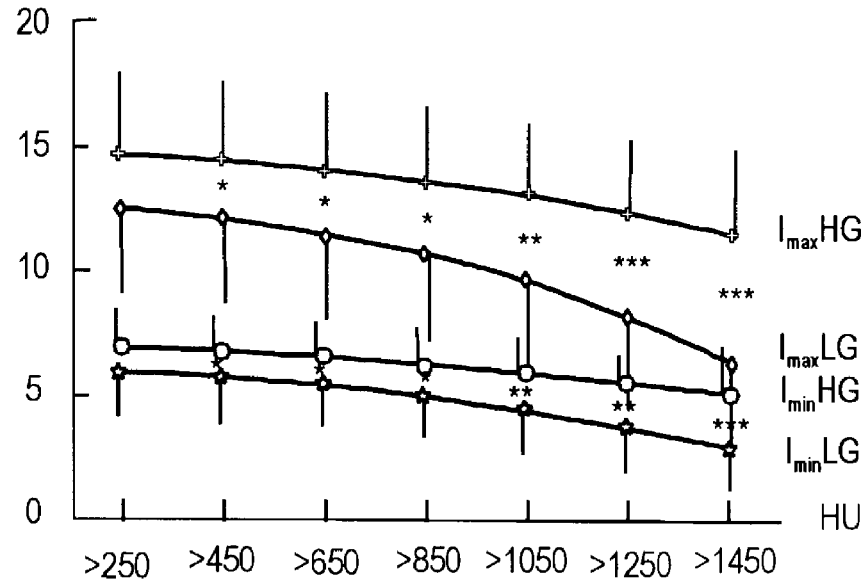

The true moments of inertia ($I^p_{ap}$, $I^p_{ml}$) and the corresponding principal moments of inertia ($I^p_{min}$, $I^p_{max}$) are shown in FIGS. 5 and 6, respectively. At section A, the low BMD group had significantly lower values for $I^P{}_{ap}$, $I^P{}_{ml}$, $I^P{}_{min}$ and $I^P{}_{max}$ at all defined bone density levels, except for $I^P{}_{ap}$ and $I^P{}_{min}$ at the >250 HU level, in comparison with the high BMD group. At section B, the differences between the low and high BMD groups also appeared significant at the high density levels.

Table 2 shows the mean values of the moments of inertia, the area moments of inertia and the scaled area moments of inertia at >750 HU level for the high and low BMD groups. The results indicate that the moments of inertia clearly distinguish the high and low BMD groups at sections A and B, while the differences in the area moments of inertia and in the scaled area moments of inertia are not significant. The results were similar even after controlling the effect of body weight by the analysis of covariance.

There were no significant differences between the high and low BMD groups at section A with respect to the principal angle R which indicates the direction of the greatest flexural rigidity (R=3.15±6.60° and R=2.36±6.78°, respectively). However, at section B, there was a significant difference in R between the high and low BMD groups (R=0.52±3.84° and R=-4.63±6.37°, respectively, p=0.008). The difference between sections A and B was greater in the low BMI) group than in the high BMD group.

The correlations between the moments of inertia and CSA and BMD are shown in Table 3. The results were similar whether body weight was taken into account or not. CSA correlated positively with $I^P{}_{ap}$, $I^P{}_{ml}$ and $I^P{}_{min}$, $I^P{}_{max}$ in both groups and at both sections. BMD correlated positively with $I^P{}_{ap}$ and $I^P{}_{min}$ only in the low BMD group. No correlations were found between BMD and CSA in either section or in either group.

TABLE 3

Correlations between moments of inertia and CSA and BMD in the groups of (r. p) high and low calcaneus BMD of 78-year-old women

| Moments of inertia | High BMD group (n = 19) | | Low BMD group (n = 17) | |
| --- | --- | --- | --- | --- |
| | CSA$_{bone}$ | BMD | CSA$_{bone}$ | BMD |
| Section A | | | | |
| $I^P{}_{ap}$ | 0.767 | 0.073 | 0.776 | 0.599 |
| | (<0.001) | (0.765) | (<0.001) | (0.011) |
| $I^P{}_{ml}$ | 0.912 | 0.235 | 0.844 | 0.344 |
| | (<0.001) | (0.333) | (<0.001) | (0.177) |
| $I^P{}_{min}$ | 0.802 | 0.066 | 0.780 | 0.583 |
| | (<0.001) | (0.789) | (<0.001) | (0.014) |
| $I^P{}_{max}$ | 0.915 | 0.240 | 0.846 | 0.356 |
| | (<0.001) | (0.322) | (<0.001) | (0.160) |

TABLE 2

THE MEAN VALUES OF THE MOMENTS OF INERTIA AT >750 HU LEVEL IN THE GROUPS OF HIGH AND LOW CALCANEUS BMD OF 78-YEAR-OLD WOMEN (MEAN ± SD, p)

| | Moments of inertia (g*mm) | | | Area moments of inertia (mm$^4$) | | | Scaled area moments of inertia (mm$^4$) | | |
| --- | --- | --- | --- | --- | --- | --- | --- | --- | --- |
| | High BMD Gr (n = 19) | Low BMD Gr (n = 17) | p | High BMD Gr (n = 19) | Low BMD Gr (n = 17) | p | High BMD Gr (n = 19) | Low BMD Gr (n = 17) | p |
| Section A | | | | | | | | | |
| $I_{ap}$ | 8798 ± 1717 | 6874 ± 2668 | 0.014 | 7494 ± 1453 | 6629 ± 2181 | 0.166 | 7459 ± 1427 | 6622 ± 2202 | 0.180 |
| $I_{ml}$ | 19689 ± 3907 | 15281 ± 4625 | 0.004 | 16527 ± 3223 | 14730 ± 4154 | 0.154 | 16692 ± 3277 | 14906 ± 4334 | 0.170 |
| $I_{min}$ | 8631 ± 1623 | 6734 ± 2635 | 0.013 | 7376 ± 1380 | 6517 ± 2179 | 0.162 | 7319 ± 1350 | 6488 ± 2189 | 0.174 |
| $I_{max}$ | 19855 ± 3904 | 15421 ± 4634 | 0.004 | 16645 ± 3226 | 14842 ± 4132 | 0.151 | 16833 ± 3274 | 15041 ± 4315 | 0.167 |
| Section B | | | | | | | | | |
| $I_{ap}$ | 6765 ± 1486 | 5637 ± 1791 | 0.047 | 6243 ± 1358 | 5534 ± 1189 | 0.429 | 5481 ± 1190 | 5193 ± 1463 | 0.519 |
| $I_{ml}$ | 14132 ± 3195 | 11346 ± 3408 | 0.016 | 11396 ± 2523 | 10502 ± 2989 | 0.337 | 11453 ± 2537 | 10563 ± 3096 | 0.350 |
| $I_{min}$ | 6731 ± 1472 | 5532 ± 1762 | 0.033 | 5511 ± 1177 | 5090 ± 1473 | 0.348 | 5453 ± 1174 | 5098 ± 1440 | 0.421 |
| $I_{max}$ | 14165 ± 3205 | 11450 ± 3421 | 0.019 | 11419 ± 2532 | 10588 ± 2994 | 0.373 | 11481 ± 2548 | 10658 ± 3108 | 0.389 |

TABLE 3-continued

Correlations between moments of inertia and CSA and BMD in the groups of (r. p) high and low calcaneus BMD of 78-year-old women

| Moments of inertia | High BMD group (n = 19) | | Low BMD group (n = 17) | |
| --- | --- | --- | --- | --- |
| | CSA$_{bone}$ | BMD | CSA$_{bone}$ | BMD |
| Section B | | | | |
| $I^P{}_{ap}$ | 0.866 | 0.045 | 0.559 | 0.468 |
| | (<0.001) | (0.853) | (0.020) | (0.058) |
| $I^P{}_{ml}$ | 0.900 | 0.106 | 0.840 | 0.152 |
| | (<0.001) | (0.666) | (<0.001) | (0.559) |
| $I^P{}_{min}$ | 0.870 | 0.060 | 0.566 | 0.458 |
| | (<0.001) | (0.809) | (0.018) | (0.065) |
| $I^P{}_{max}$ | 0.899 | 0.099 | 0.839 | 0.161 |
| | (<0.001) | (0.686) | (<0.001) | (0.538) |

Body mass correlated significantly with $I^P{}_{ml}$ (r=0.518, p=0.033 for section A, and r=0.518, p=0.033 for section B) and $I^P{}_{max}$(r=0.523, p=0.031 for section A and r=0.518, p=0.033 for section B) at both sections in the low BMD group, but not in the high BMJ group.

The middle shaft of the tibia is composed mostly of cortical bone. When women age, cortical bone is lost at the endosteal surfaces at a more rapid rate than it is gained in the periosteal surfaces, thus leading to a net reduction of as much as 30 to 50% in bone thickness. This study has shown that both densitometric and geometric properties (cross-sectional areas and true moments of inertia) of the tibia were clearly different between elderly women with high and low calcaneus BMD. The high BMD group had a higher tibia BMD and CSA as well as higher moments of inertia in comparison with the low BMD group. Our results also showed that the inner CSA had expanded more in the low BMD group, who had a smaller bone cross-sectional area in comparison to the high BMD group. Accordingly, it may be assumed that the low BMA) group has a low capacity to withstand loading on the bone. However, load carrying capacity is not only dependent on the CSA of bone but also on how the bone mass is distributed within the CSA.

Bone strength is influenced by its geometrical properties such as the moments of inertia which indicate the distribution of bone mineral around its bending axis. The moment of inertia is thus a measure of the resistance of the bone to an imposed bending load. Our results show the low BMD group to have smaller moments of inertia than the high BMD group. When using the high density values in the calculation of these quantities, the differences between the high and low BMD groups were largest for $I^p_{max}$ and $I^p_{ml}$ which reflect the properties of the tibia in the direction of greatest strength. Accordingly, our findings indicate that these two groups have a different resistance to bending, especially in the direction of greatest strength of the tibia. The low BMD group has lost more of its bone strength in comparison to the high BMD group and thus has a higher risk of fractures.

In addition to bone material and geometrical properties, fracture occurrence also depends on loading conditions and on loading history. Loading changes the configuration of deformable objects through the development of internal forces within the object. For most people, daily activity together with body weight are the principal source of external loads on bone. Although the specific loading conditions were unknown in our study, we speculate, on the basis of the differences between the groups in the history of physical activity and in body weight, that the women in the high BMD group have had more loading on bone during their earlier life time.

It has been suggested that the adaptation of the skeleton to its mechanical usage can be homeostatically regulated. Our results showed that the high BMD group had obviously adapted quite well to the mechanical usage, and that their bones have good mechanical properties. By contrast, the low BMD group had lost their tibia bone mass mainly from the anterior part of the tibia. To some degree, for maintaining the resistance of bone to bending, bone mass seems to be maintained in the periosteal area. The principal angle R, which indicates the direction of the greatest flexural rigidity of the tibia, was rotated on the average more in the low BMD group than in the high BMD group. It seems that the altered distribution of bone mass results from nonhomogeneous changes, and only takes place in some parts of bones, although the factors; which control the location of the biomechanical requirements are still unknown. The redistribution of bone mass compensates for the loss in bone material strength, and thus the supportive function and its resistance to bending of bone are better maintained.

In reality, since bone mass is not homogeneously distributed, the true mass and its distribution should be taken into account in determining e.g. the moments of inertia. A previous study on sex differences in geometry of femoral neck with aging, by using a Lunar DP3 scanner in vivo, found that BMC and CSA decreased with age in both sexes, but only females showed a decline in the cross-sectional moment of inertia (area moment of inertia), resulting from a combination of greater bone loss and less compensatory geometric restructuring with age. However, from the data it can be seen that the differences in area moment of inertia between the sexes are mainly due to the big difference in the CSA between the sexes. Since it is cross-sectional type of study, it is also impossible to evaluate the restructuring of the geometric features. In fact, we found that if the bone mass and its distribution were not taken into account, such as when area or scaled moments of inertia were estimated, the results did not distinguish between high and low BMD groups. Accordingly, the results suggest that the differences which exist between the high and low BMD groups are best revealed by the calculation of bone mass together with its distribution within the cross section.

In general, levels which exceed 250 HU are considered to correspond to compact bone: However, in the case of moments of inertia, the 250 HU level may be too low for distinguishing the differences between different groups. If a person has a large CSA with a low density, she or he may have a moment of inertia similar to that of a person who has a small CSA with a high density. Therefore, to distinguish between these two cases, it is necessary to use different threshold values for bone density in determining the moments of inertia of bone. The differences between different subjects become more pronounced when only the high density areas are included.

Moreover, a recent study in 235 cortical specimens of cadavers aged 20–102 years showed that changes in the porosity of cortical bone accounted for 76 percent of the reduction in strength, while mineral content which meant ash-weight percentage and Ca++ weight of bone did not show associations with strength decline.

In conclusion, our results suggest that both the density and mass distribution of the tibia were clearly different between the low and high BMD women. The differences in cross-sectional mass and its distribution were more pronounced when only the high density areas were included. Moreover, for predictive purposes the true distribution of bone mass should be taken into account in determining the moments of inertia. Determination of the cross-sectional mass distribution of bone combined with BMD should have a better discriminatory capability than BMD only in studying bone strength and fracture risk.

Although the invention has been described by reference to a specific embodiment, it should be understood that numerous changes may be made within the spirit and scope of the inventive concepts described. Accordingly, it is intended that the invention not be limited to the described embodiment, but that it have the full scope defined by the language of the following claims.

What is claimed is:

1. A method for diagnosing and monitoring osteoporosis characterized by the steps of:

obtaining volumetric bone mineral density and cross-sectional area information of a bone of a patient utilizing computerized tomography;

displaying the information in matrix image form wherein each pixel indicates the density of the bone tissue in the image area at that point;

distinguishing pixels depicting bone tissue from the rest of the image utilizing a lower-limit criteria;

calculating density and mass distribution of bone tissue over the image meeting and exceeding the criteria; and quantifying a condition of the patient's bone tissue as a function of the calculated density and mass distribution of bone tissue.

2. The method of claim 1 characterized in that calculating the density and mass distribution includes quantifying the surface-area moment of inertia of the bone weighted for density.

3. The method of claim 2 characterized in that quantifying the surface-area moment of inertia includes calculating moments of inertia of the bone in the principal anatomic directions of the bone, anterior-posterior and medial-lateral.

4. The method of claim 2 characterized in that calculating the density and mass distribution includes calculating the principal, maximum and minimum, moments of inertia of the bone.

5. The method of claim 1 characterized in that calculating the mass distribution includes calculating the polar mass distribution of the bone.

6. The method of claim 1 characterized in that calculating the mass distribution includes calculating the annular mass distribution.

7. The method of claim 1 characterized in that the bone is a tibia of the patient.

8. The method of claim 1 characterized in that the bone is a femur of the patient.

* * * * *